US007702399B2

(12) United States Patent
Heil et al.

(10) Patent No.: US 7,702,399 B2
(45) Date of Patent: Apr. 20, 2010

(54) SUBCUTANEOUS ELECTRODE AND LEAD WITH PHORESIS BASED PHARMACOLOGICAL AGENT DELIVERY

(75) Inventors: Ron Heil, Roseville, MN (US); Paul A. Haefner, Circle Pines, MN (US); Adam W. Cates, Minneapolis, MN (US); Darrell Orvin Wagner, Isanti, MN (US); Curtis Charles Lindstrom, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 29 days.

(21) Appl. No.: 10/728,072

(22) Filed: Dec. 4, 2003

(65) Prior Publication Data

US 2004/0230274 A1     Nov. 18, 2004

Related U.S. Application Data

(60) Provisional application No. 60/462,272, filed on Apr. 11, 2003.

(51) Int. Cl.
    *A61N 1/05*      (2006.01)
(52) U.S. Cl. .......................................... 607/120; 607/3
(58) Field of Classification Search ................. 607/129, 607/20, 119, 148, 33, 120, 3, 9, 1; 606/41; 604/20–21
See application file for complete search history.

(56) References Cited

U.S. PATENT DOCUMENTS

| | | | |
|---|---|---|---|
| 3,941,122 A | | 3/1976 | Jones |
| 4,146,029 A | * | 3/1979 | Ellinwood, Jr. .......... 604/891.1 |
| 4,506,680 A | * | 3/1985 | Stokes ........................ 607/120 |
| 4,562,841 A | | 1/1986 | Brockway et al. |
| 4,819,661 A | | 4/1989 | Heil, Jr. et al. |
| 4,819,662 A | | 4/1989 | Heil, Jr. et al. |
| 4,917,104 A | * | 4/1990 | Rebell ........................ 600/585 |
| 4,953,551 A | | 9/1990 | Mehra et al. |
| 5,020,544 A | | 6/1991 | Dahl et al. |
| 5,036,849 A | | 8/1991 | Hauck et al. |
| 5,041,107 A | | 8/1991 | Heil, Jr. |
| 5,090,422 A | | 2/1992 | Dahl et al. |
| 5,133,353 A | | 7/1992 | Hauser |
| 5,170,784 A | | 12/1992 | Ramon et al. |
| 5,179,945 A | | 1/1993 | Van Hofwegen et al. |
| 5,203,348 A | | 4/1993 | Dahl et al. |

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—George R Evanisko
*Assistant Examiner*—Michael Kahelin
(74) *Attorney, Agent, or Firm*—Hollingsworth & Funk, LLC

(57) ABSTRACT

An implantable subcutaneous device includes a lead and electrode for cardiac monitoring and intervention. The device has an implantable lead including a lead body, a subcutaneous electrode supported by the lead body and a pharmacological agent impelled from the device using phoresis. The pharmacological agent provides a therapeutic treatment to subcutaneous non-intrathoracic tissue. A method of implanting subcutaneous leads involves providing a lead including a lead body, a subcutaneous electrode, and a pharmacological agent and using phoresis to impel the pharmacological agent into subcutaneous non-intrathoracic tissue surrounding the lead.

42 Claims, 9 Drawing Sheets

U.S. PATENT DOCUMENTS

| | | | |
|---|---|---|---|
| 5,209,229 A | 5/1993 | Gilli | |
| 5,230,337 A | 7/1993 | Dahl et al. | |
| 5,261,400 A | 11/1993 | Bardy | |
| 5,282,785 A * | 2/1994 | Shapland et al. | 604/21 |
| 5,284,136 A | 2/1994 | Hauck et al. | |
| 5,292,338 A | 3/1994 | Bardy | |
| 5,300,108 A | 4/1994 | Dahl et al. | |
| 5,301,677 A | 4/1994 | Hsung | |
| 5,313,953 A | 5/1994 | Yomtov et al. | |
| 5,314,430 A | 5/1994 | Bardy | |
| 5,314,459 A | 5/1994 | Swanson et al. | |
| 5,324,324 A | 6/1994 | Vachon et al. | |
| 5,331,966 A | 7/1994 | Bennett et al. | |
| 5,360,442 A | 11/1994 | Dahl et al. | |
| 5,366,496 A | 11/1994 | Dahl et al. | |
| 5,372,606 A | 12/1994 | Lang et al. | |
| 5,376,106 A | 12/1994 | Stahmann et al. | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,405,362 A | 4/1995 | Kramer et al. | |
| 5,411,031 A | 5/1995 | Yomtov | |
| 5,411,525 A | 5/1995 | Swanson et al. | |
| 5,411,539 A | 5/1995 | Neisz | |
| 5,439,482 A | 8/1995 | Adams et al. | |
| 5,441,518 A | 8/1995 | Adams et al. | |
| 5,449,370 A | 9/1995 | Vaitekunas | |
| 5,468,254 A | 11/1995 | Hahn et al. | |
| 5,531,779 A | 7/1996 | Dahl et al. | |
| 5,545,202 A | 8/1996 | Dahl et al. | |
| 5,603,732 A | 2/1997 | Dahl et al. | |
| 5,620,466 A | 4/1997 | Haefner et al. | |
| 5,628,730 A * | 5/1997 | Shapland et al. | 604/21 |
| 5,634,938 A | 6/1997 | Swanson et al. | |
| 5,641,326 A | 6/1997 | Adams | |
| 5,662,688 A | 9/1997 | Haefner et al. | |
| 5,683,447 A | 11/1997 | Bush et al. | |
| 5,697,953 A | 12/1997 | Kroll et al. | |
| 5,704,365 A | 1/1998 | Albrecht et al. | |
| 5,724,984 A | 3/1998 | Arnold et al. | |
| 5,749,909 A * | 5/1998 | Schroeppel et al. | 607/33 |
| 5,788,979 A | 8/1998 | Alt et al. | |
| 5,807,306 A * | 9/1998 | Shapland et al. | 604/21 |
| 5,827,326 A | 10/1998 | Kroll et al. | |
| 5,843,017 A | 12/1998 | Yoon | |
| 5,895,414 A | 4/1999 | Sanchez-Zambrano | |
| 5,916,243 A | 6/1999 | KenKnight et al. | |
| 5,957,956 A | 9/1999 | Kroll et al. | |
| 5,987,746 A | 11/1999 | Williams | |
| 5,989,208 A | 11/1999 | Nita | |
| 5,997,497 A | 12/1999 | Nita et al. | |
| 6,044,298 A | 3/2000 | Salo et al. | |
| 6,055,454 A | 4/2000 | Heemels | |
| 6,099,567 A | 8/2000 | Badylak et al. | |
| 6,134,470 A | 10/2000 | Hartlaub | |
| 6,144,879 A * | 11/2000 | Gray | 607/20 |
| 6,148,230 A | 11/2000 | KenKnight | |
| 6,167,305 A | 12/2000 | Cammilli et al. | |
| 6,168,801 B1 | 1/2001 | Heil, Jr. et al. | |
| 6,178,349 B1 * | 1/2001 | Kieval | 607/3 |
| 6,214,017 B1 | 4/2001 | Stoddard et al. | |
| 6,280,462 B1 | 8/2001 | Hauser et al. | |
| 6,282,444 B1 * | 8/2001 | Kroll et al. | 607/3 |
| 6,295,474 B1 * | 9/2001 | Munshi | 607/121 |
| 6,304,786 B1 * | 10/2001 | Heil et al. | 607/126 |
| 6,309,355 B1 | 10/2001 | Cain et al. | |
| 6,322,532 B1 | 11/2001 | D'Sa et al. | |
| 6,360,129 B1 | 3/2002 | Ley et al. | |
| 6,361,531 B1 | 3/2002 | Hissong | |
| 6,361,780 B1 | 3/2002 | Ley et al. | |
| 6,409,675 B1 | 6/2002 | Turcott | |
| 6,413,216 B1 | 7/2002 | Cain et al. | |
| 6,415,174 B1 | 7/2002 | Bebehani et al. | |
| 6,416,510 B1 * | 7/2002 | Altman et al. | 606/41 |
| 6,436,068 B1 | 8/2002 | Bardy | |
| 6,438,410 B2 | 8/2002 | Hsu et al. | |
| 6,475,232 B1 | 11/2002 | Babbs et al. | |
| 6,478,776 B1 | 11/2002 | Rosenman et al. | |
| 6,480,733 B1 | 11/2002 | Turcott | |
| 6,491,639 B1 | 12/2002 | Turcott | |
| 6,500,121 B1 | 12/2002 | Slayton et al. | |
| 6,512,940 B1 | 1/2003 | Brabec et al. | |
| 6,522,915 B1 | 2/2003 | Ceballos et al. | |
| 6,524,251 B2 | 2/2003 | Rabiner et al. | |
| 6,564,106 B2 | 5/2003 | Guck et al. | |
| 6,584,363 B2 | 6/2003 | Heil, Jr. et al. | |
| 6,607,509 B2 | 8/2003 | Bobroff et al. | |
| 6,615,083 B2 | 9/2003 | Kupper | |
| 6,622,046 B2 | 9/2003 | Fraley et al. | |
| 6,695,781 B2 | 2/2004 | Rabiner et al. | |
| 6,837,888 B2 | 1/2005 | Ciarrocca et al. | |
| 6,958,040 B2 | 10/2005 | Oliver et al. | |
| 7,190,997 B1 * | 3/2007 | Darvish et al. | 607/3 |
| 7,204,820 B2 | 4/2007 | Akahoshi | |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035380 A1 | 3/2002 | Rissmann et al. | |
| 2002/0035381 A1 | 3/2002 | Bardy et al. | |
| 2002/0042629 A1 | 4/2002 | Bardy et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0049476 A1 | 4/2002 | Bardy et al. | |
| 2002/0052636 A1 | 5/2002 | Bardy et al. | |
| 2002/0068958 A1 | 6/2002 | Bardy et al. | |
| 2002/0072773 A1 | 6/2002 | Bardy et al. | |
| 2002/0082658 A1 | 6/2002 | Heinrich et al. | |
| 2002/0091414 A1 | 7/2002 | Bardy et al. | |
| 2002/0095184 A1 | 7/2002 | Bardy et al. | |
| 2002/0103510 A1 | 8/2002 | Bardy et al. | |
| 2002/0107544 A1 | 8/2002 | Ostroff et al. | |
| 2002/0107545 A1 | 8/2002 | Rissmann et al. | |
| 2002/0107546 A1 | 8/2002 | Ostroff et al. | |
| 2002/0107547 A1 | 8/2002 | Erlinger et al. | |
| 2002/0107548 A1 | 8/2002 | Bardy et al. | |
| 2002/0107549 A1 | 8/2002 | Bardy et al. | |
| 2002/0107559 A1 | 8/2002 | Sanders et al. | |
| 2002/0120299 A1 | 8/2002 | Ostroff et al. | |
| 2002/0138123 A1 | 9/2002 | Casas-Bejar et al. | |
| 2002/0193784 A1 | 12/2002 | McHale et al. | |
| 2003/0004546 A1 | 1/2003 | Casey | |
| 2003/0004552 A1 | 1/2003 | Plombon et al. | |
| 2003/0023175 A1 | 1/2003 | Arzbaecher et al. | |
| 2003/0032943 A1 | 2/2003 | Topaz | |
| 2003/0036778 A1 | 2/2003 | Ostroff et al. | |
| 2003/0040698 A1 | 2/2003 | Makin et al. | |
| 2003/0045904 A1 | 3/2003 | Bardy et al. | |
| 2003/0069609 A1 | 4/2003 | Thompson | |
| 2003/0073949 A1 | 4/2003 | Giammarusti | |
| 2003/0088278 A1 | 5/2003 | Bardy et al. | |
| 2003/0088279 A1 | 5/2003 | Rissmann et al. | |
| 2003/0088280 A1 | 5/2003 | Ostroff | |
| 2003/0088281 A1 | 5/2003 | Ostroff et al. | |
| 2003/0088282 A1 | 5/2003 | Ostroff | |
| 2003/0088283 A1 | 5/2003 | Ostroff | |
| 2003/0088286 A1 | 5/2003 | Ostroff et al. | |
| 2003/0097153 A1 | 5/2003 | Bardy et al. | |

2003/0212436 A1    11/2003  Brown

OTHER PUBLICATIONS

Theofilos M. Kolettis, Md, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212(1970).

Karel Smits & Marek Malik, *Defibrillation Threshold (DFT) Model of a Fully Subcutaneous ICD System*, Europace Supplements, vol. 2, Jun. 2001 at col. 778, p. B83.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

Wikipedia, "Anabolic Steroid", Aug. 20, 2006.

Smith et al., "Analysis of Chromameter Results Obtained from Corticosteroid-Induced Skin Blanching", Pharmaceutical Research, col. 15, No. 2, Abstract Only (1998).

Gilron et al., "Preemptive Analgesic Effects of Steroid Anesthesia with Alphaxalone in the Rat Formalin Test", Anesthesiology, Mar. 1996, 84(3), 1996.

Demling et al., "The Rate of Restoration of Body Weight after Burn Injury, Using the Anabolic Agent Oxandrolone, is Not Age Dependent", Burns, Feb. 2001, 27(1), Abstract only, 2001.

\* cited by examiner

SUBCUTANEOUS ELECTRODE AND LEAD WITH PHORESIS BASED PHARMACOLOGICAL AGENT DELIVERY

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to subcutaneously implantable cardiac cardioverters/defibrillators and monitors, and, more particularly, to subcutaneously implantable leads and device components that impel pharmacological agents using phoresis.

BACKGROUND OF THE INVENTION

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators (ICDs) include one or more endocardial leads to which at least one defibrillation electrode is connected. Such ICDs are capable of delivering high-energy shocks to the heart, interrupting a ventricular tachyarrythmia or ventricular fibrillation, and allowing the heart to resume normal sinus rhythm. ICDs may also include pacing functionality.

Although ICDs are effective at preventing Sudden Cardiac Death (SCD), most people at risk of SCD are not provided with implantable defibrillators. The primary reasons for this unfortunate reality include the limited number of physicians qualified to perform transvenous lead/electrode implantation, a limited number of surgical facilities adequately equipped to accommodate such cardiac procedures, and a limited number of the at-risk patient population that can safely undergo the required endocardial or epicardial lead/electrode implant procedure. Subcutaneous ICDs are being developed to address these and other issues.

SUMMARY OF THE INVENTION

The present invention is directed to subcutaneous cardiac devices and components, and methods of using same to improve patient comfort, reduce morbidity, and improve surgical outcomes by incorporating pharmacological agents that are actively impelled into tissue using phoresis. According to one embodiment, a cardiac device has an implantable lead including a lead body, a subcutaneous electrode supported by the lead body, and a pharmacological agent provided on the lead and/or electrode. The pharmacological agent is impelled into subcutaneous non-intrathoracic tissue using phoresis. In another embodiment, an implantable cardioverter/defibrillator system includes a can to which an implantable lead is coupled. One or more pharmacological agents may be provided on the lead, electrode, can, or combination of these components and impelled phoretically into surrounding tissue.

An embodiment of the present invention is directed to impelling a plurality of pharmacological agents disposed on a lead and/or an electrode into tissue using phoresis. Pharmacological agents may be provided on one or more electrodes alone or in combination with pharmacological agents on the can and/or lead body, all of which are impelled into surrounding tissue using phoresis.

A method of implanting subcutaneous leads is directed to providing a lead including a lead body, a subcutaneous electrode, and a pharmacological agent, and delivering the pharmacological agent to subcutaneous non-intrathoracic tissue using phoresis. The method may include providing a sheath and inserting the lead into the sheath to deliver the lead into subcutaneous non-intrathoracic tissue.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
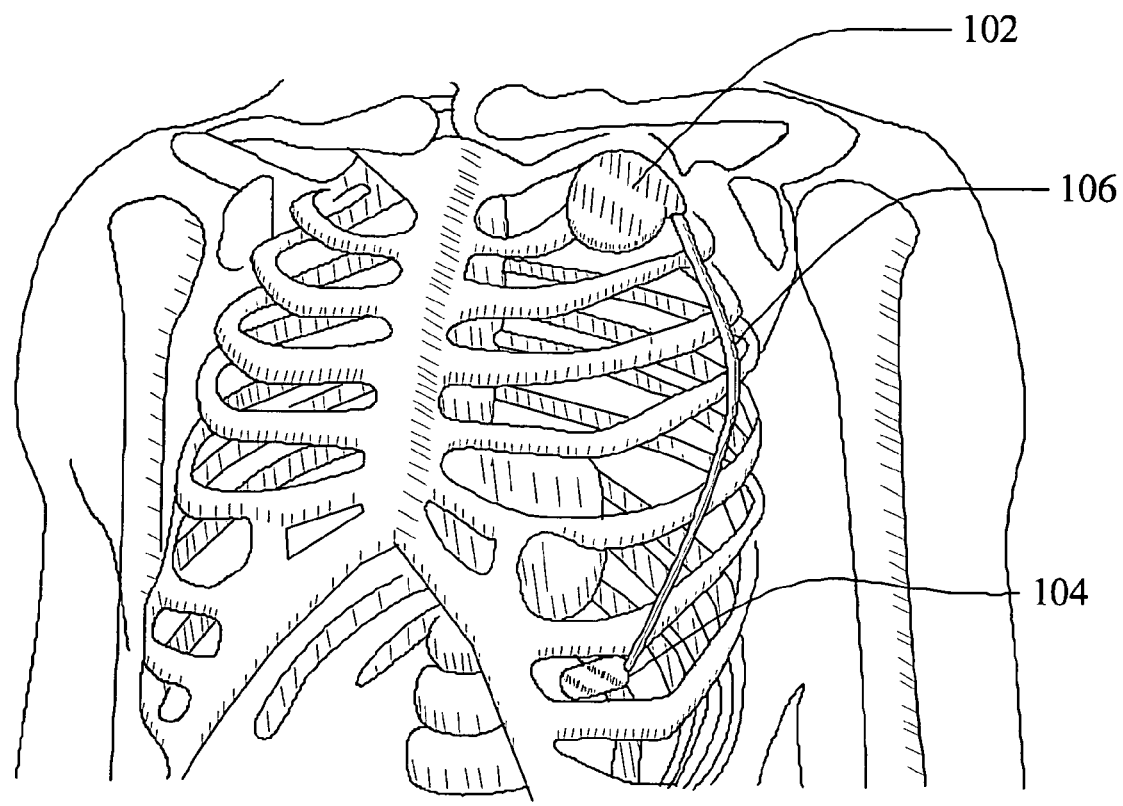
FIGS. 1A and 1B are views of a transthoracic cardiac sensing and/or stimulation device as implanted in a patient.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

A device employing an implantable lead implemented in accordance with the present invention may incorporate one or more of the features, structures, methods, or combinations thereof described herein below. For example, a subcutaneous cardiac monitor or stimulator may be implemented to include a lead and other components having one or more of the advantageous features and/or processes described below. It is intended that such a device or method need not include all of the features and functions described herein, but may be implemented to include selected features and functions that provide for unique structures and/or functionality.

In general terms, an implantable lead implemented in accordance with the present invention may be used with a subcutaneous cardiac monitoring and/or stimulation device. One such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in contact with, the heart, great vessel or coronary vasculature.

In another implementation, one or more leads incorporating electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Figure 1B:
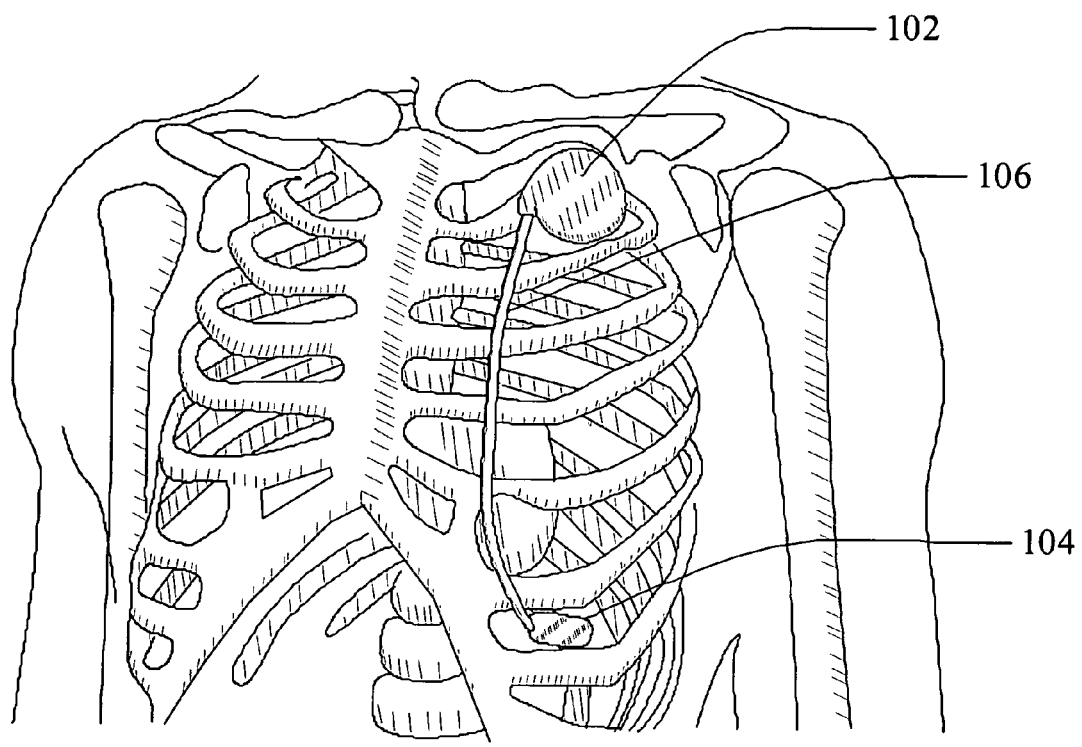

Referring now to FIGS. 1A and 1B of the drawings, there is shown a configuration of a transthoracic cardiac sensing and/or stimulation (ITCS) device implanted in the chest region of a patient at different locations by use of a dissection tool. In the particular configuration shown in FIGS. 1A and 1B, the ITCS device includes a housing 102 within which various cardiac sensing, detection, processing, and energy delivery circuitry may be housed. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed. An ITCS system according to this approach is distinct from conventional approaches in that it may be configured to include a combination of two or more electrode subsystems that are implanted subcutaneously.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible. In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and the subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have, for example, an arcuate or angled shape.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly, or both the housing 102 and the rigid electrode support assembly. Alternatively, a mechanical/electrical coupler may be used to establish mechanical and electrical connections between the rigid electrode support assembly and the housing 102. In such a configuration, a variety of different electrode support assemblies of varying shapes, sizes, and electrode configurations can be made available for physically and electrically connecting to a standard ITCS device.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst the subcutaneous electrodes 104. Accordingly, subcutaneous leads of the present invention may be shaped appropriately for specific electrodes or families of electrodes and electrode support assemblies.

Figure 2A:
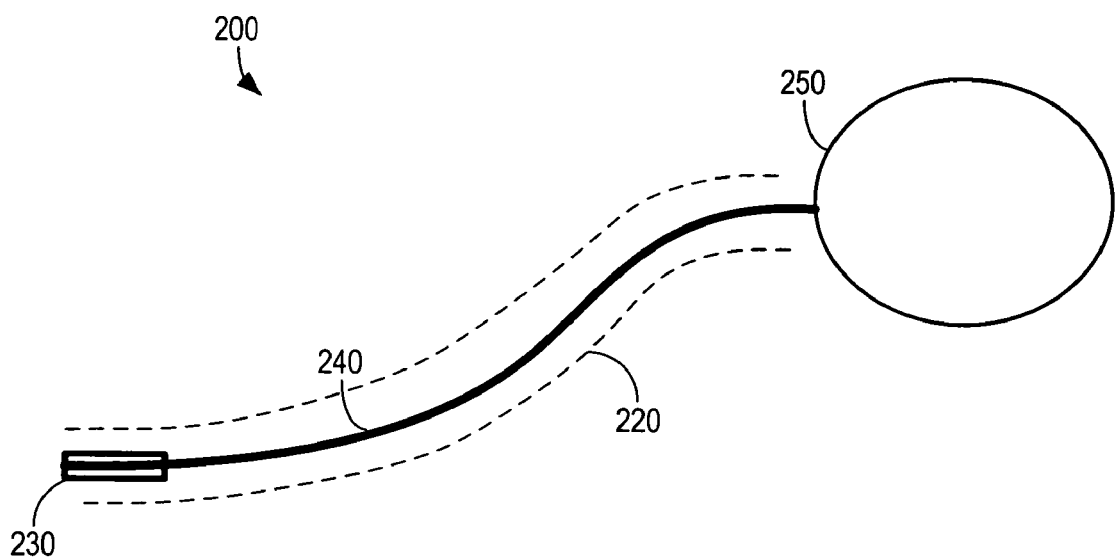
FIG. 2A illustrates a lead in accordance with the present invention, inserted in a dissected subcutaneous path extending from the can.

Referring now to FIG. 2A, an ITCS system 200 is illustrated including a can 250 with a lead 240 inserted into a dissection path 220. The lead 240 includes an electrode 230, here illustrated at the distal end of the lead 240. The dissection path 220 lies within the subcutaneous tissue of a patient as illustrated in FIGS. 1A and 1B.

Figure 2B:
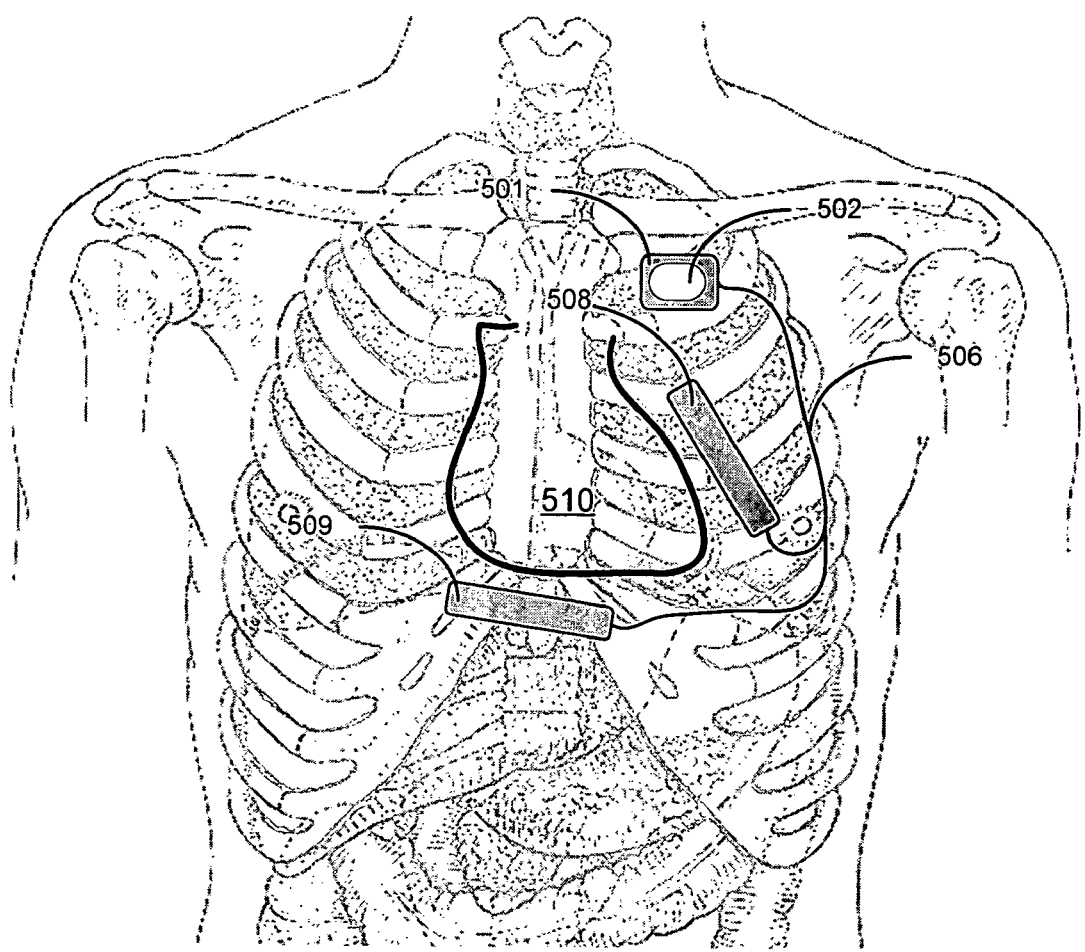
FIG. 2B illustrates various components of a transthoracic cardiac sensing and/or stimulation device in accordance with embodiments of the present invention.

Referring to FIG. 2B, a can electrode 502 is positioned on a housing 501 that encloses the ITCS device electronics. In one embodiment, the can electrode 502 includes the entirety of the external surface of housing 501. In other embodiments, various portions of the housing 501 may be electrically isolated from the can electrode 502 or from tissue. For example, the active area of the can electrode 502 may include all or a portion of either the anterior or posterior surface of the housing 501 to direct current flow in a manner advantageous for cardiac sensing and/or stimulation.

The housing 501 may resemble that of a conventional implantable ICD, and may be approximately 20-100 cc in volume, with a thickness of 0.4 to 2 cm and with a surface area on each face of approximately 30 to 100 cm². As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include coatings formed from silicone rubber, polyurethane, polyvinylidene fluoride, or parylene, for example.

In addition, or alternatively, all or portions of the housing 501 may be treated to change the electrical conductivity characteristics thereof for purposes of optimally directing current flow. Various known techniques can be employed to modify the surface conductivity characteristics of the housing 501, such as by increasing or decreasing surface conductivity, to optimize current flow. Such techniques may include mechanically or chemically altering the surface of the housing 501 to achieve desired electrical conductivity characteristics.

In the configuration shown in FIG. 2B, the ITCS device housing 501 containing the electronics (i.e., the can) is not used as an electrode. In this case, an electrode system comprising two electrode subsystems 508, 509 coupled to the housing 501 may be implanted subcutaneously in the chest region of the body, such as in the anterior thorax. The first and the second electrode subsystems 508, 509 are placed in opposition with respect to the ventricles of a heart 510, with the majority of the ventricular tissue of the heart 510 included within a volume defined between the electrode subsystems 508, 509. As illustrated in FIG. 2B, the first electrode system 508 is positioned superior to the heart 510 relative to a superior aspect of the heart 510, e.g., parallel to the left ventricular free wall. The second electrode system 509 is located inferior to the heart 510 and positioned in relation to an inferior aspect of the heart 510, e.g., parallel to the right ventricular free wall. A cable or wiring 506 conductively couples the electrode subsystems 508, 509 to the housing 501.

In this configuration, the first and the second electrode subsystems 508 and 509 may include any combination of electrodes used for sensing and/or electrical stimulation. In various configurations, the electrode subsystems 508, 509 may each include a single electrode or a combination of electrodes. The electrode or electrodes in the first and second electrode subsystems 508, 509 may include any combination of one or more coil electrodes, tip electrodes, ring electrodes, multi-element coils, spiral coils, spiral coils mounted on non-conductive backing, and screen patch electrodes, for example.

Figure 3:
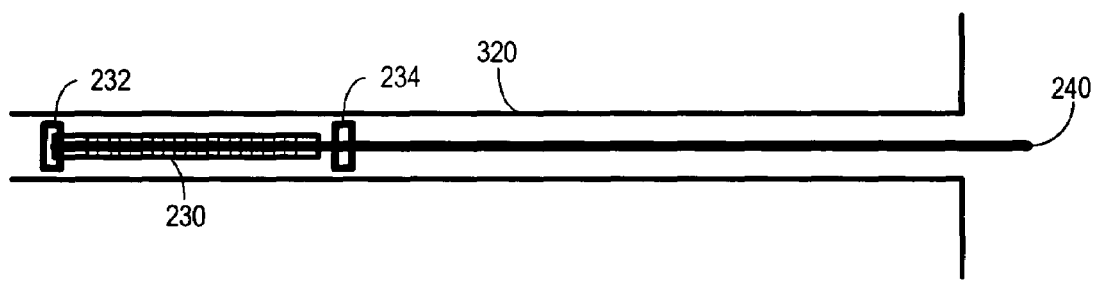
FIG. 3 is a plan view of a lead incorporating phoresis based delivery of pharmacological agents in accordance with the present invention, enclosed within a sheath.

The lead 240, shown in FIG. 2A, and/or the electrode subsystems 508, 509, shown in FIG. 2B, may be inserted into the dissection path 220 (FIG. 2A) without use of an introducer sheath, or may alternatively be inserted with use of a sheath 320 as illustrated in FIG. 3. In FIG. 3, the lead 240 extends from the sheath 320, with the electrode 230 enclosed within the lumen of the sheath 320. The electrode 230 is illustrated with pharmacological agents 232 and 234 at the distal end and proximal end respectively.

Still referring to FIG. 3, the pharmacological agents 232 and 234 may be incorporated with the lead 240 via, for example, a collar, a porous region, a coating, or other suitable arrangement. The lead 240 may be inserted into the dissection path 220 (FIG. 2A) inside the sheath 320. After proper location within the subcutaneous tissue, the sheath 320 may be stripped away from the electrode 230, revealing the pharmacological agents 232 and 234 to the surrounding tissue. A period of pharmacological activity may be initiated by impelling pharmacological agents 232 and 234 into the tissue surrounding the lead 240 using phoresis such as, in the example illustrated in FIG. 3, electrophoresis.

Two non-limiting examples of phoresis are electrophoresis and sonophoresis. Electrophoresis is generally understood as an electrochemical process in which colloidal particles and/or macromolecules with a net electric charge migrate under the influence of an electric potential. For purposes herein, electrophoresis is synonymous with ionophoresis, iontophoresis, and dielectrolysis.

Sonophoresis is generally understood as a sonochemical process in which colloidal particles and/or macromolecules migrate under the influence of pressure waves, such as continuous wave or burst-mode ultrasound. For purposes herein, sonophoresis is synonymous with sontophoresis. Phoresis based technologies such as, for example, electrophoresis and sonophoresis, may be used in accordance with the present invention to impel pharmacological agents into tissue.

A non-limiting, non-exhaustive list of suitable pharmacological agents 232 and 234 includes analgesics, anesthetics, antibiotics, antiseptics, steroids, anti-inflammatory drugs, agents that promote hemostasis, agents that provide vasoconstriction, collagen, and agents that increase the rate of healing. A non-exhaustive, non-limiting list of pharmacological activities includes: antisepsis, antibiosis, analgesia, anesthesia, vasoconstriction, and hemostasis.

Suitable analgesics or anesthetics may be, for example, aspirin, IBUPROFEN, BUPIVACAINE, LIDOCAINE, MAPRIVACAINE and PROCAINE. Suitable steroids may be, for example, DEXAMETHASONE and BETAMETHASONE. A suitable pharmacological agent that provides vasoconstriction may be, for example, EPINEPHRINE. Suitable antibiotics or antiseptics may be, for example, VANCOMYCIN and CEFALOZIN. A suitable pharmacological agent to increase the rate of healing may be, for example, stomach submucosa derived tissue, such as that disclosed in U.S. Pat. No. 6,099,567 and incorporated herein by reference, which may be impregnated with one or more pharmacological agents.

Figure 4:
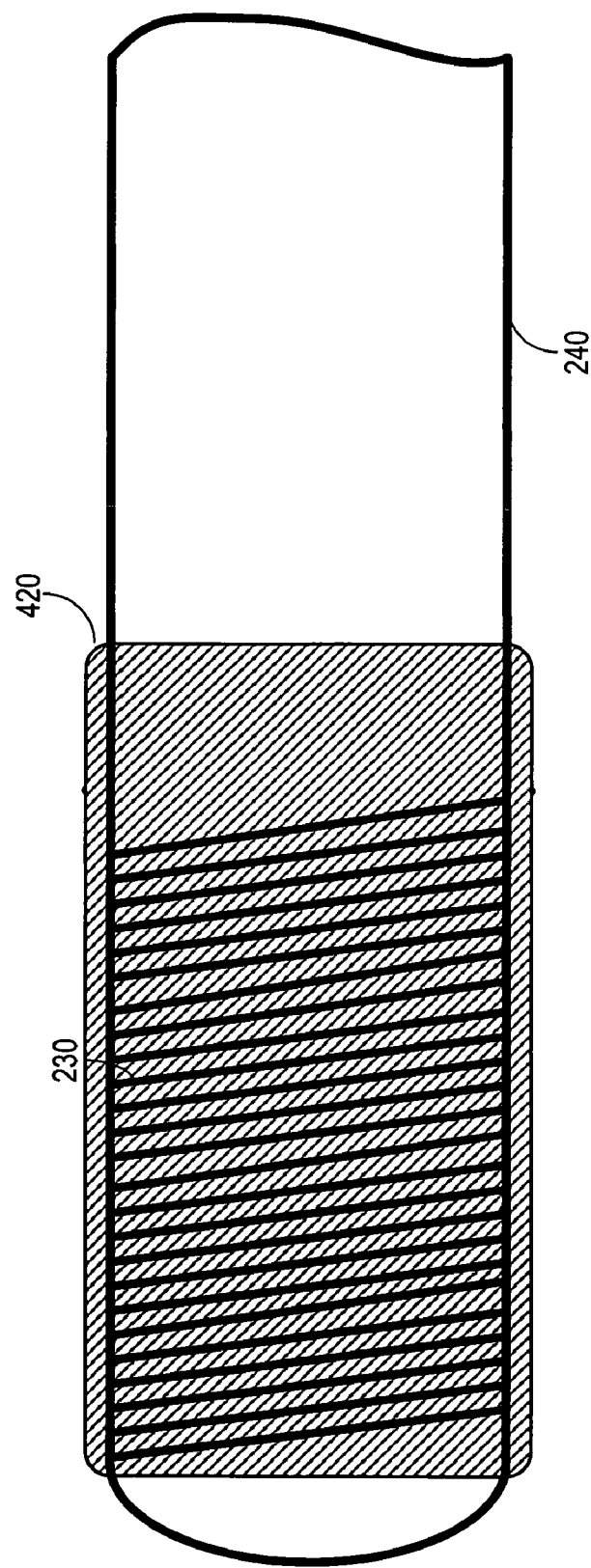
FIG. 4 is a magnified view of a lead with an electrode configured to facilitate phoresis based delivery of pharmacological agents in accordance with the present invention.

FIG. 4 illustrates the lead 240 with an electrode 230 and a coating 420. The coating 420 contains the pharmacological agent desired near the distal end of the lead 240. The coating 420 may be placed on the lead 240 by, for example, painting, spraying, dipping, vapor deposition, or other suitable arrangement. Pharmacological agents in the coating 420 may be impelled using electrophoresis, as described earlier.

Figure 5A:
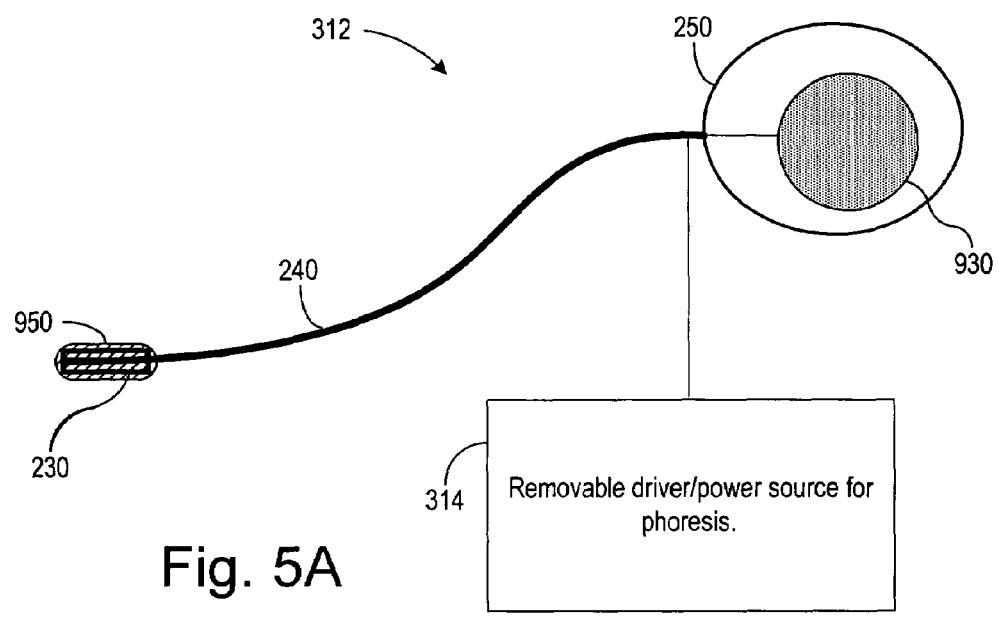
FIG. 5A is a top view of an embodiment of a system configured to facilitate phoresis based delivery of pharmacological agents in accordance with the present invention.

FIG. 5A illustrates a method for phoresis delivery of a pharmacological agent from a system 312 without using the can's power source, thereby conserving energy stored in the energy source disposed in the can 250. In the embodiment shown in FIG. 5A, the can 250 incorporates a pharmacological agent delivery arrangement 930 disposed on the can 250. The embodiment of FIG. 5A is further shown to include a tiered pharmacological delivery arrangement 950 disposed on the electrode 230.

The arrangement 930 may partially or completely cover or coat the can 250. For example, the arrangement 930 may cover the entire first surface of the can 250, but only cover 25% of a second surface to provide a large uncoated area of the second surface to act as an active electrode for cardiac stimulation therapy. The second surface of the can 250 may be positioned relative to the heart to optimize energy delivery and directivity. The pharmacological delivery arrangements 930 and 950 may be placed by, for example, painting, spraying, dipping, vapor deposition, or other suitable approach. The pharmacological delivery arrangements 930, 950 may include any combination of pharmacological activities or agents such as, for example, pharmacological activities and agents described previously.

In another configuration, the can 250 may be equipped with a reservoir (seen as element 930 disposed on the can 250) within which a pharmacological agent or agents can be stored. The reservoir 930 may include a single chamber or multiple chambers for storing one or more pharmacological agents or other fluid useful for facilitating phoresis delivery of a pharmacological agent. The reservoir 930 of the can 250 may be fluidly connected to a surface of the can 250 in a configuration in which phoresis delivery of a pharmacological agent is implemented using the can 250. An exit port on the surface of the can 250, through which the pharmacological agent passes, may be treated or coated to enhance delivery of the pharmacological agent from the surface of the can 250.

Alternatively, or in addition, the reservoir 930 of the can 250 may be fluidly connected to the electrode 230 via a lumen of the lead 240. In this configuration, a pharmacological agent may be transported from the reservoir 930 of the can 250 to the electrode via the lumen to facilitate phoresis delivery of a pharmacological agent from the electrode 250. A micropump or other pressure generating arrangement may be employed in accordance with this configuration to facilitate transport of the pharmacological agent through the lumen of the lead 240.

During and/or after the implantation process, an external driver 314 may be attached to the system 312. The external driver 314 provides power and control of the phoretic impelling of the pharmacological agent during the implantation process. The external driver 314 may be incorporated into a dissection device, so that phoresis may be accomplished during the dissection and implantation of the system.

One approach to delivering pharmacological agents using external driver 314 employs the existing electrodes and wiring of the ITCS system for phoresis delivery. For example, the external driver 314 may use the can 250 as a ground, grounding the patient, and may use the electrode 230 to initiate an electric potential between the electrode 230 and the grounded tissue, and impelling the pharmacological agent from the delivery arrangement 950 using electrophoresis. In this approach, the external driver 314 may be simply an external power supply, such that no power is used from the implantable components for phoresis during or acutely after implantation.

In another embodiment, the external driver 314 may be grounded to the patient using a ground pad, such as ground pads used for electrosurgery. In this arrangement, both the lead 240, including electrode 230, and the can 250 may be used as potential sources for phoresis. The external driver 314 may include a power supply as well as driving electronics.

Figure 5B:
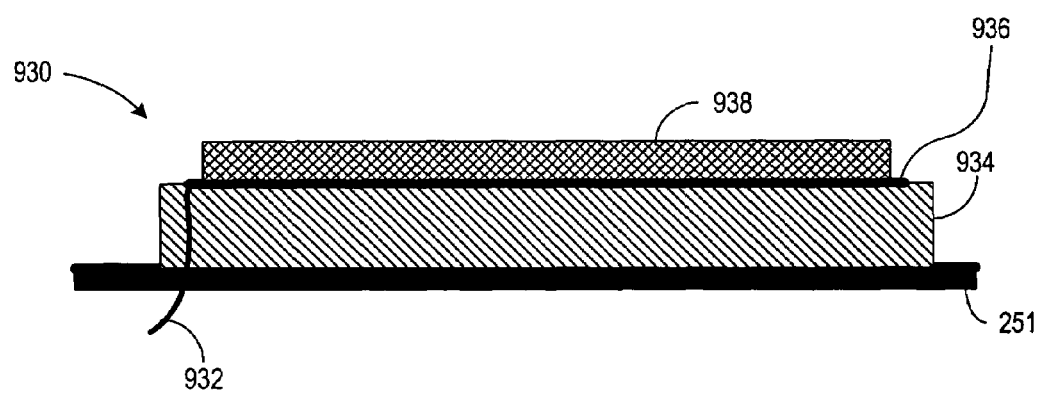
FIG. 5B is a magnified side view of a portion of the can illustrated in FIG. 5A, the can having a polyvinylidene fluoride (PVDF) coating used to facilitate phoresis based delivery of pharmacological agents in accordance with the present invention.

Referring now to FIG. 5B, an embodiment of the present invention provides for sonophoresis using the delivery arrangement 930. In FIG. 5B, delivery arrangement 930 may be, for example, a layer of polyvinylidene fluoride, designated PVDF layer 934. The PVDF layer 934 is a piezoelectric polymer, where applying an electric field across the polymer causes the polymer to expand or contract, based on polarity of the electric potential.

The PVDF layer 934 may have a conducting surface coating 936 that acts as a capacitor plate, storing electric charge to create an electric field across the PVDF layer 934. Illustrated in the side view of FIG. 5B, a housing 251 of the can 250 (seen in FIG. 5A) may act as a ground electrode, and the conducting surface coating 936 may act as a source electrode. A wire 932 may provide the electrical potential to the conducting surface coating 936. A pharmacological agent 938 may be disposed on the exterior surface of the conducting surface coating 936.

Applying an electric field, such as by use of conducting surface coating 936 on the PVDF layer 934, creates an ultrasonic transducer. The PVDF layer 934 of delivery arrangement 930 may be used to generate an acoustic field that impels pharmacological agents using sonophoresis. The conducting surface coating 936 may also be useful as an electrode for driving the pharmacological agent 938 using electrophoresis.

An alternating current (AC) signal may be applied to the conducting surface coating 936 using wire 932. The AC signal creates an alternating electric field across the PVDF layer 934, causing the PVDF layer 934 to expand and contract, producing an ultrasonic field capable of driving the pharmacological agent 938 using sonophoresis. A direct current (DC) signal may additionally, or alternately, be applied to the conducting surface coating 936 using wire 932. The DC signal may create an electric field in the tissue capable of driving the pharmacological agent 938 using electrophoresis. Electrophoresis and sonophoresis may occur simultaneously, individually, or alternatingly as desired.

For example, it may be beneficial to phoretically impel an analgesic in coordination with a defibrillation therapy during the entire useful life of the system 312 (FIG. 5A), to mitigate some of the discomfort from the therapy. The delivery arrangement 930 may be activated by the defibrillation therapy itself, or may be activated independently before, during, or after any therapy delivery. The therapy itself may impel the analgesic using electrophoresis and/or the delivery arrangement 930 may impel the analgesic using sonophoresis. Illustrated here, and as described also in previous embodiments, combinations of pharmacological activity provided with ITCS devices may provide significantly improved outcomes, less morbidity, and improved patient comfort and acceptance.

Additional details of dissection devices for implantation of subcutaneous systems and implantable devices that may be employed or adapted to drive phoretic systems or provide phoresis are disclosed in commonly owned U.S. Patent Publication No. 2004/0204734; U.S. Patent Publication No. 2004/0204735; U.S. Pat. No. 7,529,592; and U.S. Pat. No. 7,566,318 which are hereby incorporated herein by reference.

Figure 6:
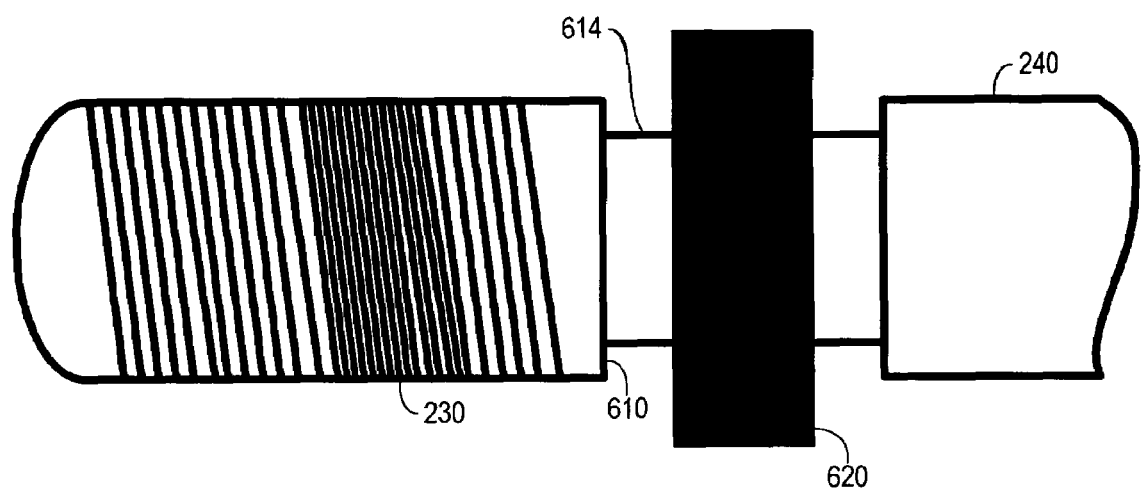
FIG. 6 is a magnified view of an embodiment of a lead configured to facilitate phoresis based delivery of pharmacological agents in accordance with the present invention.

FIG. 6 illustrates another embodiment of the present invention. In FIG. 6, the lead 240 is shown to have a groove 610 providing a fixation point for a collar 620. Collar 620 may be, for example, a silicone collar impregnated with a pharmacological agent. Collars impregnated with pharmacological agents are known in the art such as, for example, collars described in U.S. Pat. No. 6,361,780 hereby incorporated herein by reference. Although the width of groove 610 is illustrated in FIG. 6 to be significantly larger than the width of the collar 620, any desirable fit may be provided.

In FIG. 6, a potential surface 614 is located beneath the collar 620. The potential surface 614 may be an electrical conductor to provide a source of electrical potential for electrophoresis, and/or may be a source for other forms of phoresis such as, for example, an ultrasonic transducer for sonophoresis as described above.

Figure 7:
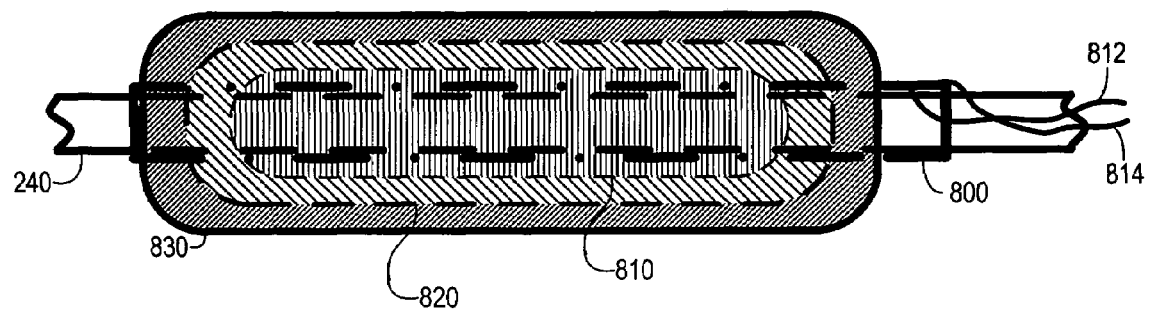
FIG. 7 is a magnified view of another embodiment of a lead configured to facilitate phoresis based delivery of pharmacological agents in accordance with the present invention.

Referring now to FIG. 7, a three layer tiered pharmacological delivery method is illustrated. The lead 240 is illustrated having a first layer 810, a second layer 820, and a third layer 830 on the lead 240. The lead 240 is further shown to include a pair of conductors 812, 814 coupled to a phoretic element 800, such as a PVDF layer or other phoresis delivery arrangement. The conductors 812, 814 may be coupled to contacts or conductors of a driver or power source, such as driver/power source 314 shown in FIG. 5A, for example.

The layers 810, 820, and 830 are configured such that the pharmacological agent in the third layer 830 is delivered first as the third layer 830 is impelled away and the pharmacological agent delivers its activity. After the third layer 830 is effectively removed, the second layer 820 is revealed. The pharmacological agent in the second layer 820 is delivered second as the second layer 820 is impelled away and the pharmacological agent delivers its activity. After the second layer 820 is effectively removed, the first layer 810 is revealed. The pharmacological agent in the first layer 810 is delivered last as the first layer 810 is impelled away and the pharmacological agent delivers its activity. The layers 810, 820, and 830 may, for example, be continuously or discretely applied at one or more locations along the length of the lead 240. One or more drugs may be disposed within each of the layers 810, 820 and 830.

Figure 8:
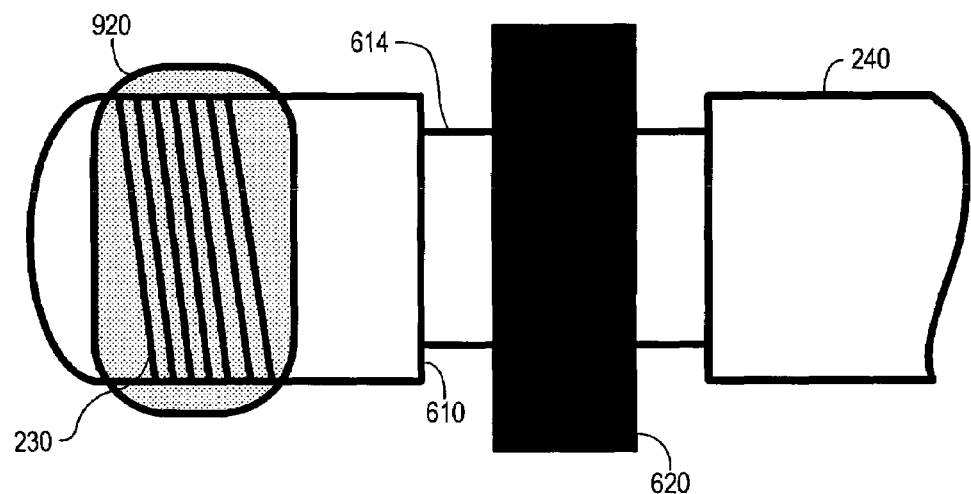
FIG. 8 is a magnified view of another embodiment of a lead with an electrode configured to facilitate phoresis based delivery of pharmacological agents in accordance with the present invention.

FIG. 8 illustrates an embodiment of the present invention that differs from FIG. 6 by the addition of a coating 920 applied over the electrode 230. It may be advantageous to provide a pharmacological delivery to the area of tissue surrounding the electrode 230 of the subcutaneous lead 240. For example, the electrode coating 920 may include an analgesic that is adapted to be quickly delivered from the electrode 230 using phoresis. This approach provides for an acute reduction in post-operative pain, while not hindering the electrical capabilities of the electrode 230 for use soon after the lead 240 is placed into the dissected tissue. The electrode coating 920 may be used as the only pharmacological delivery arrangement, and/or may be used in combination with other pharmacological delivery arrangements such as the collar 620 illustrated in FIG. 8 and/or the delivery arrangements illustrated in FIG. 7 or other arrangements disclosed herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable cardiac system, comprising:
   a cardiac electrode, the electrode configured for subcutaneous placement within a patient and for one or both of cardiac monitoring and cardiac electrical stimulation;
   an implantable can;
   a pharmacological agent provided along an exterior surface of the implantable can;
   a power source; and
   a driving arrangement coupled to the can, the driving arrangement comprising a polyvinylidene fluoride layer and a conducting surface coating along the polyvinylidene fluoride layer and said driving arrangement in electrical connection with the power source, the driving arrangement configured to provide sonophoresis delivery of the pharmacological agent from the exterior surface along which the pharmacological agent is provided to subcutaneous tissue by power source electrical activation of the conducting surface coating causing movement of the polyvinylidene fluoride layer.

2. The system according to claim 1, further comprising a rigid elongated support structure coupled to the can, wherein the cardiac electrode is provided on the rigid elongated support structure.

3. The system according to claim 2, wherein the rigid elongated support structure is configured to maintain the cardiac electrode and a second electrode on the can in opposition with respect to the ventricles of the heart.

4. The system according to claim 1, further comprising an implantable pharmacological agent reservoir within the can.

5. The system according to claim 4, further comprising a micro-pump configured to facilitate transport of the pharmacological agent from the reservoir to the exterior surface along which the pharmacological agent is provided.

6. The system according to claim 1, wherein the driving arrangement is configured to generate an acoustic field that impels the pharmacological agent into subcutaneous tissue.

7. The system according to claim 1, wherein the pharmacological agent is disposed along the conducting surface coating.

8. The system according to claim 1, wherein the housing serves as an electrical ground for the driving arrangement.

9. The system according to claim 1, wherein the driving arrangement is configured to generate an ultrasonic field that drives the pharmacological agent into subcutaneous tissue.

10. The system according to claim 1, further comprising a controller configured to coordinate phoresis delivery of the pharmacological agent relative to electrical cardiac stimulation therapy such that the driving arrangement facilitates phoresis delivery of the pharmacological agent after delivery of electrical cardiac stimulation therapy.

11. The system according to claim 1, further comprising a controller configured to coordinate phoresis delivery of the pharmacological agent relative to electrical cardiac stimulation therapy such that the driving arrangement facilitates phoresis delivery of the pharmacological agent before delivery of electrical cardiac stimulation therapy.

12. The system according to claim 1, wherein the pharmacological agent is disposed on the polyvinylidene fluoride layer.

13. The system according to claim 1, wherein the driving arrangement is configured to deliver an AC signal alternating at an ultrasonic frequency to the conducting surface coating to provide sonophoresis delivery of the pharmacological agent.

14. The system according to claim 1, wherein the driving arrangement is configured to deliver a DC bias voltage with an AC signal alternating at an ultrasonic frequency to the conducting surface coating to provide sonophoresis delivery of the pharmacological agent.

15. An implantable system, comprising:
a can;
a pharmacological agent provided on a portion of an exterior surface of the can;
a power source;
a can electrode, the electrode configured for subcutaneous non-intrathoracic placement within a patient and for one or both of cardiac monitoring and cardiac electrical stimulation; and
a driving arrangement in electrical connection with the power source and coupled to the can, the driving arrangement comprising a polyvinylidene fluoride layer and a conducting surface coating along the polyvinylidene fluoride layer, the driving arrangement configured to provide sonophoresis delivery of the pharmacological agent from at least the portion of the exterior surface of the can to subcutaneous tissue by power source electrical activation of the conducting surface coating and movement of the polyvinylidene fluoride layer.

16. The system according to claim 15, wherein the driving arrangement is configured to generate an acoustic field that impels the pharmacological agent into subcutaneous, non-intrathoracic tissue.

17. The system according to claim 15, wherein the driving arrangement is configured to generate an ultrasonic field that drives the pharmacological agent into subcutaneous, non-intrathoracic tissue.

18. The system according to claim 15, further comprising an implantable pharmacological agent reservoir and a micropump configured to facilitate transport of pharmacological agent from the reservoir to the exterior surface of the can.

19. The system according to claim 15, wherein the pharmacological agent is disposed along the conducting surface coating.

20. The system according to claim 15, wherein the at least part of the driving arrangement comprises an external driver detachably coupled to the can, the external driver configured to provide power and control for phoresis delivery of the pharmacological agent during surgical implantation of the can.

21. The system according to claim 15, wherein the can comprises a porous region on the portion of the exterior surface, the pharmacological agent at least partially filling pores of the porous region.

22. The system according to claim 21, wherein the porous region comprises a doped polymer matrix.

23. The system according to claim 15, further comprising a lead body coupled to the can, wherein the lead body and the can form a rigid unitary structure having an arcuate shape.

24. The system according to claim 23, wherein the coating covers at least 25% of a surface area of the can.

25. The system according to claim 15, further comprising a lead coupled to the can, the lead comprising an electrode and a rigid elongated support structure configured to stabilize and maintain a spacing between the electrode and the implantable can in subcutaneous, non-intrathoracic tissue within the patient.

26. The system according to claim 15, further comprising a controller configured to coordinate phoresis delivery of the pharmacological agent relative to electrical cardiac stimulation therapy such that the driving arrangement facilitates phoresis delivery of the pharmacological agent after delivery of electrical cardiac stimulation therapy.

27. The system according to claim 15, further comprising a controller configured to coordinate phoresis delivery of the pharmacological agent relative to electrical cardiac stimulation therapy such that the driving arrangement facilitates phoresis delivery of the pharmacological agent before delivery of electrical cardiac stimulation therapy.

28. An implantable cardiac lead system, comprising:
a lead body having a ground layer;
a cardiac electrode coupled to the lead body, the electrode configured for subcutaneous placement in a patient and for one or both of cardiac monitoring and cardiac electrical stimulation;
an implantable can coupled to the lead body;
one or more conductors coupled to the electrode and disposed within the lead body;
a pharmacological agent provided along one or both of the can and a longitudinal portion of an exterior surface of the lead body over the ground layer;
a power source; and
means, in electrical connection with the power source, for impelling the pharmacological agent into subcutaneous tissue using sonophoresis, wherein the impelling means comprises a polyvinylidene fluoride layer and a conducting surface coating along the polyvinylidene fluoride layer, and the polyvinylidene fluoride layer and the conducting surface coating are provided along one or both of the can and the longitudinal portion of the lead body along which the pharmacological agent is provided.

29. The lead system according to claim 28, wherein the impelling means comprises means for impelling the pharmacological agent using sonophoresis by electrical activation of the conducting surface coating causing movement of the polyvinylidene fluoride layer.

30. The lead system according to claim 28, further comprising a controller configured to coordinate phoresis delivery of the pharmacological agent relative to electrical cardiac stimulation therapy such that the driving arrangement facilitates sonophoresis delivery of the pharmacological agent after delivery of electrical cardiac stimulation therapy.

31. The lead system according to claim 28, wherein the lead body comprises a rigid elongated support structure configured to stabilize and maintain a spacing between the cardiac electrode and the implantable can in subcutaneous, non-intrathoracic tissue within the patient.

32. A system, comprising:
an implantable medical device, comprising:
a can that houses circuitry configured to provide one or both of cardiac monitoring and cardiac stimulation;

a lead coupled to the can, the lead comprising a lead body, a cardiac electrode coupled to the lead body, a ground layer, and one or more conductors coupled to the cardiac electrode and disposed within the lead body, the electrode configured for subcutaneous placement within a patient and for one or both of cardiac monitoring and cardiac electrical stimulation;

a first pharmacological agent provided along at least a longitudinal portion of an exterior surface of the lead body; and a second pharmacological agent provided on a portion of an exterior surface of the can; and a driver apparatus detachably coupled to the implantable medical device, the driver apparatus comprising a power source and a plurality of polyvinylidene fluoride layers and a plurality of conducting surface coatings each disposed along respective polyvinylidene fluoride layers of the plurality of polyvinylidene fluoride layers, the driver apparatus configured to facilitate sonophoresis delivery of at least one of the first pharmacological agent from the longitudinal portion of the exterior surface of the lead body over the ground layer and the second pharmacological agent from the portion of the exterior surface of the can by power source electrical activation of the conducting surface coatings and movement of the polyvinylidene fluoride layers.

33. The system according to claim 32, wherein the lead comprises an rigid elongated support structure configured to stabilize and maintain a spacing between the cardiac electrode and the can in subcutaneous, non-intrathoracic tissue within the patient.

34. The system according to claim 33, wherein the lead and the can form a unitary structure having an arcuate shape.

35. The system according to claim 33, wherein the rigid elongated support structure is configured to maintain the cardiac electrode and a second electrode disposed on the can in opposition with respect to the ventricles of the heart.

36. The system according to claim 32, wherein the polyvinylidene fluoride layers and the conducting surface coatings are provided at least along the longitudinal portion of the exterior surface of the lead body.

37. The system according to claim 32, wherein the driver apparatus is configured to deliver an AC signal alternating at an ultrasonic frequency to the conducting surface coatings to provide sonophoresis delivery.

38. The system according to claim 32, wherein the driver apparatus is configured to deliver a DC bias voltage with an AC signal alternating at an ultrasonic frequency to the conducting surface coatings to provide sonophoresis delivery.

39. The system according to claim 32, further comprising a controller configured to coordinate phoresis delivery of the pharmacological agent relative to electrical cardiac stimulation therapy such that the driver apparatus facilitates phoresis delivery of the pharmacological agent after delivery of electrical cardiac stimulation therapy.

40. The system according to claim 32, further comprising a controller configured to coordinate phoresis delivery of the pharmacological agent relative to electrical cardiac stimulation therapy such that the driver apparatus facilitates phoresis delivery of the pharmacological agent before delivery of electrical cardiac stimulation therapy.

41. The system according to claim 32, further comprising an implantable pharmacological agent reservoir within the can.

42. The system according to claim 41, further comprising a micro-pump configured to facilitate transport of pharmacological agent from the reservoir to the exterior surface of the lead body and the exterior surface of the can.

* * * * *